US006241719B1

(12) United States Patent
Wallace et al.

(10) Patent No.: US 6,241,719 B1
(45) Date of Patent: Jun. 5, 2001

(54) METHOD FOR FORMING A RADIOACTIVE STENT

(75) Inventors: George Wallace, Coto de Caza, CA (US); Richard J. Greff, St. Pete Beach, FL (US)

(73) Assignee: Micro Therapeutics, Inc., Irvine, CA (US)

( * ) Notice: Subject to any disclaimer, the term of this patent is extended or adjusted under 35 U.S.C. 154(b) by 0 days.

(21) Appl. No.: 09/311,802

(22) Filed: May 13, 1999

(51) Int. Cl.$^7$ ................................................. A61M 31/00
(52) U.S. Cl. .................................. 604/509; 600/4; 623/1; 604/103.02; 604/103.01
(58) Field of Search ................................ 600/3, 4; 623/1; 424/424, 425, 472, 476, 1.33; 606/192, 194; 604/101.01, 103.01, 13.02, 509, 913

(56) References Cited

U.S. PATENT DOCUMENTS

| | | |
|---|---|---|
| Re. 36,370 | 11/1999 | Li . |
| 3,527,224 | 9/1970 | Rabinowitz, et al. . |
| 3,592,676 | 7/1971 | Hawkins, et al. . |
| 4,938,763 | 7/1990 | Dunn et al. . |
| 5,213,580 | 5/1993 | Slepian et al. . |
| 5,458,568 | 10/1995 | Racchini et al. ........................ 604/19 |
| 5,580,568 | 12/1996 | Greff et al. . |
| 5,634,946 | 6/1997 | Slepian . |
| 5,667,767 | 9/1997 | Greff et al. . |
| 5,674,287 | 10/1997 | Slepian et al. . |
| 5,749,915 | 5/1998 | Slepian . |
| 5,749,922 | 5/1998 | Slepian et al. . |
| 5,800,538 | 9/1998 | Slepian et al. . |
| 5,843,156 | 12/1998 | Slepian et al. . |
| 5,914,345 | 6/1999 | Slepian et al. . |
| 5,921,954 | 7/1999 | Mohr, Jr. et al. . |
| 5,947,977 | 9/1999 | Slepian et al. . |
| 6,007,833 | 12/1999 | Chudzik et al. . |

OTHER PUBLICATIONS

"Cancer, Principles & Practice of Oncology, " 4$^{th}$ Ed., vol. 1, *Cancer Treatment*, pp. 545–548 (1993);.

Castaneda–Zuniga, et al., *Interventional Radiology*, in Vascular Embolotherapy, Part 1, 1:9–32, Williams & Wilkins, Publishers (1992);.

Kinugasa, et al., "Direct Thrombosis of Aneurysms with Cellulose Acetate Polymer," *J. Neurosurgery*, 77:501–507 (1992);.

Kinugasa, et al., "Early Treatment of Subarachnoid Hemorrhage After Preventing Rerupture of an Aneurysm," *J. Neurosurgery*, 83:34–41 (1995);.

Kinugasa, et al., "Prophylactic Thrombosis to Prevent New Bleeding and to Delay Aneurysm Surgery," *Neurosurgery*, 36:661–667 (1995);.

Laird, et al., "Inhibition of Neointimal Proliferation With Low–Dose Irradiation From a β–Particle Emitting Stent," *Circulation* 93(3):529–536 (1996);.

Taki, et al., "Selection and Combination of Various Endovascular Techniques in the Treatment of Giant Aneurysms," *J. Neurosurgery*, 77:37–42 (1992).

Slepian, Polymeric Endoluminal Paving: A Family of Evolving Methods for Extending Endoluminal Therapeutics Beyond Stenting, *Contemporary Interventional Techniques*, 12(4):715–737.

Slepian et al., $\beta_3$–Integrins Rather Than $\beta_1$–Integrins Dominate Integrin–Matrix Interactions Involving in Postinjury Smooth Muscle Cell Migration, *American Heart Assoication*, pp. 1818–1827, May 12, 1998.

Slepian et al., Pre–Conditioning of Smooth Muscle Cells via Induction of the Heat Shock Response Limits Proliferation Following Mechanical Injury, *Biochem. and Biophys. Research Commun.*, 225:600–607 (1996).

Hill–West, et al., Inhibition of Thrombosis and Intimal Thickening by in situ Photopolymerization of Thin Hydrogel Barriers, *Proc. Natl. Acad. Sci. USA*, 91:5967–5971, Jun. 1994.

Slepian, Polymeric Endoluminal Gel Paving: Therapeutic Hydrogel Barriers and Sustained Drug Delivery Depots for Local Arterial Wall Biomanipulation, *Semin Intervent Cardiol*, 1:103–116 (1996).

Schopohl, et al., $^{192}$IR Endovascular Brachytherapy for Avoidance of Intimal Hyperplasia after Percutaneous Transluminal Angioplasty and Stent Implantation in Peripheral Vessels: 6 Years of Experience, *Int. J. Radiation Oncology Biol. Phys.*, 36(4):835–840 (1996).

Fischell, et al., The Beta–Particle–Emitting Radioisotope Stenet (Isostent): Animal Studies and Planned Clinical Trials, *The Am J. Cardiol*, 78(3A):45–50 (1996).

Fischell, et al., Low–Dose, β–Particle Emission from 'Stent' Wire Results in Complete Localized Inhibition of Smooth Muscle Cell Proliferation, *Circulation*, 90(6):2956–2963 (1994).

Waksman, Local Catheter–Based Intracoronary Radiation Therapy for Restenosis, *Am J Cardiol*, 78(3A):23–28 (1996).

Popowski, et al., Intra–Arterial$^{90}$Y Brachytherapy: Preliminary Dosimetric Study Using A Specially Modified Angioplasty Balloon, *Int J Radiation Oncology Biol Phys*, 33(3):713–717 (1995).

*Primary Examiner*—Anhtuan T. Nguyen
(74) *Attorney, Agent, or Firm*—Burns Doane Swecker & Mathis LLP

(57) ABSTRACT

Disclosed are methods for the endovascular formation of a radioactive stent using a radioactive composition. These compositions are delivered to one or more vascular sites in a mammal as a fluid composition which solidifies in vivo to form a solid, coherent radioactive mass, preferably in the form or a stent. The solidified mass stents the vascular site thereby delivering the radioactivity attendant with the composition resulting in inhibition of restenosis.

27 Claims, No Drawings

METHOD FOR FORMING A RADIOACTIVE STENT

BACKGROUND OF THE INVENTION

1. Field of the Invention

This invention is directed to methods for forming a radioactive stent at a vascular site by use of radioactive compositions. Specifically, these methods entail the in vivo delivery of radioactive compositions which are delivered as a fluid to one or more vascular sites. Subsequent solidification of this composition at the vascular site results in the formation of a stent which also acts to deliver a controlled amount of radiation to the vascular site.

In one embodiment, the fluidic radioactive compositions employed in the methods of this invention comprise a biocompatible polymer, a biocompatible solvent and a radioactive agent which provides a sufficient dose of radiation to inhibit restenosis. In another embodiment, the fluidic radioactive compositions employed in the methods of this invention comprise a biocompatible prepolymer, a radioactive agent and optionally a biocompatible solvent which provides a sufficient dose of radiation to inhibit restenosis.

REFERENCES

The following publications are cited in this application as superscript numbers:

[1] Dunn, et al., U.S. Pat. No. 4,938,763 for "Biodegradable In-Situ Forming Implants and Methods of Producing Same", issued Jul. 3, 1990

[2] Kinugasa, et al., "Direct Thrombois of Aneurysms with Cellulose Acetate Polymer", *J. Neurosurg.*, 77:501–507 (1992)

[3] "CANCER, Principles & Practice of Oncology", 4th Ed., Volume 1, "Cancer Treatment", pp. 545–548 (1993)

[4] Greff, et al., U.S. Pat. No. 5,667,767, for "Novel Compositions for Use in Embolizing Blood Vessels", issued Sep. 16, 1997

[5] Greff, et al., U.S. Pat. No. 5,580,568 for "Cellulose Diacetate Compositions for Use in Embolizing Blood Vessels", issued Dec. 3, 1996

[6] Kinugasa, et al., "Early Treatment of Subarachnoid Hemorrhage After Preventing Rerupture of an Aneurysm", *J. Neurosurg.*, 83:34–41 (1995)

[7] Kinugasa, et al., "Prophylactic Thrombosis to Prevent New Bleeding and to Delay Aneurysm Surgery", *Neurosurg.*, 36:661 (1995)

[8] Taki, et al., "Selection and Combination of Various Endovascular Techniques in the Treatment of Giant Aneurysms", *J. Neurosurg.*, 77:37–24 (1992)

[9] Evans, et al., U.S. patent application Ser. No. 08/802,252 for "Novel Compositions for Use in Embolizing Blood Vessels", filed Feb. 19, 1997

[10] Castaneda-Zuniga, et al., *Interventional Radiology*, in Vascular Embolotherapy, Part 1, 1:9-32, Williams & Wilkins, Publishers (1992)

[11] Rabinowitz, et al., U.S. Pat. No. 3,527,224 for "Method of Surgically Bonding Tissue Together", issued Sep. 8, 1970

[12] Hawkins, et al., U.S. Pat. No. 3,591,676 for "Surgical Adhesive Compositions", issued Jul. 6, 1971

[13] Laird, et al., "Inhibition of Neointimal Proliferation With Low-Dose Irradiation From a β-Particle Emitting Stent," *Circulation* 93(3):529–536 (1996)

[14] Greff, et al., U.S. Pat. No. 6,015,541 Radioactive Embolizing Compositions, issued on Jan. 18, 2000.

All of the above publications are herein incorporated by reference in their entirety to the same extent as if each individual reference was specifically and individually indicated to be incorporated herein by reference in its entirety.

2. State of the Art

Atherosclerosis, a disorder involving thickening and hardening of the wall portions of the larger arteries of mammals, is a life-threatening affliction that is largely responsible for coronary artery disease, aortic aneurysm and arterial disease of the lower extremities. Atherosclerosis also plays a major role in cerebral vascular disease. It is responsible for more deaths in the United States than any other disease.

Angioplasty has heretofore been a widely used method for treating atherosclerosis. Percutaneous transluminal coronary angioplasty (hereinafter "PTCA") procedures involve inserting a deflated balloon catheter through the skin and into the vessel or artery containing the stenosis. The catheter is then passed through the lumen of the vessel until it reaches the stenotic region, which is characterized by a build up of fatty streaks, fibrous plaques and complicated lesions on the vessel wall, which result in a narrowing of the vessel and blood flow restriction. In order to overcome the harmful narrowing of the artery caused by the atherosclerotic condition, the balloon is inflated, thus flattening the plaque against the arterial wall and otherwise expanding the arterial lumen.

Although PTCA has produced excellent results and low complication rates, there has, however, been difficulties associated with the use of this technique. In particular, during the expansion of the balloon against the arterial wall, the arterial wall is frequently damaged and injured. While this damage itself is not believed to be particularly harmful to the health or the life of the patient, the healing response triggered by this damage can cause a reoccurrence of the atherosclerotic condition. In particular, it has been observed that the smooth muscle cells associated with the stenotic region of the artery initiate cell division in response to direct or inflammatory injury of the artery.

Restenosis is the closure of a peripheral or coronary artery following trauma to the artery caused by efforts to open an occluded portion of the artery, such as, for example, by dilation, ablation, atherectomy or laser treatment of the artery. For these angioplasty procedures, restenosis occurs at a rate of about 20–50% depending on the vessel location, lesion length and a number of other variables. Restenosis is believed to be a natural healing reaction to the injury of the arterial wall that is caused by angioplasty procedures. The healing reaction begins with the clotting of blood at the site of the injury. The final result of the complex steps of the healing process is intimal hyperplasia, the migration and proliferation of medial smooth muscle cells, until the artery is again stenotic or occluded.

In an attempt to prevent restenosis, metallic intravascular stents have been permanently implanted in coronary or peripheral vessels. The stent is typically inserted by catheter into a vascular lumen and expanded into contact with the diseased portion of the arterial wall, thereby providing internal support for the lumen. However, it has been found that restenosis can still occur with such stents in place. Also, the stent itself can cause undesirable local thrombosis. To address the problem of thrombosis, persons receiving stents also receive extensive systemic treatment with anticoagulant and antiplatelet drugs.

Prior attempts to inhibit restenosis of coronary arteries have included, among other things, the use of various light therapies, chemotherapeutic agents, stents, atherectomy devices, hot and cold lasers, as well as exposure of the stenotic site to radiation. These therapies have had a varying degree of success, however, certain disadvantages are associated with each of these therapies. Although radiation therapy has shown promise, particularly in inhibiting intimal hyperplasia, the devices available for delivery of radiation sources to a stenotic site have been limited and have tended to suffer from drawbacks which limit their usefulness (see for example, U.S. Pat. No. 5,899,882). Accordingly, there is a need for a stent device which effectively delivers radiation to a stenotic or vascular site to inhibit restenosis.

SUMMARY OF THE INVENTION

This invention is directed to methods for the endovascular formation of a radioactive stent using a radioactive composition. These compositions are delivered to one or more vascular sites in a mammal as a fluid composition which solidifies in vivo to form a solid, coherent radioactive mass, preferably in the form or a stent. The solidified mass stents the vascular site thereby delivering the radioactivity attendant with the composition resulting in inhibition of restenosis.

Accordingly, in one of its method aspects, this invention is directed to a method for endovascular formation of a radioactive stent at a vascular site which method comprises:

(a) endovascularly delivering to a vascular site a liquid permeable balloon catheter, said balloon cathether comprising a balloon membrane at least a portion of which is liquid permeable;

(b) inflating said balloon to contact the vascular walls at said vascular site by delivering thereto a composition, said composition comprising a biocompatible polymer, a biocompatible solvent and a water insoluble radioisotope; and (c) in situ forming a radioactive stent at the vascular site by maintaining positive pressure on said balloon wherein at least a portion of said composition permeates through said permeable balloon membrane into the vascular site whereupon the composition forms a solid mass which contacts and adheres to the vascular walls thereby forming a radioactive stent at said vascular site.

Preferably the radioactive fluid composition employed in this aspect of the methods of this invention comprises:

(a) a biocompatible polymer;

(b) a biocompatible solvent; and (c) from about 0.1 to about 35 weight percent of a water insoluble radioisotope having a radioactive content of from about 0.1 microcuries to about 35 microcuries.

The biocompatible polymer employed in these compositions and methods can be either a biodegradable polymer or a non-biodegradable polymer but is, preferably, a non-biodegradable polymer.

In another aspect of this invention, the biocompatible polymer can be replaced with a biocompatible prepolymer and, when so used, the presence of the biocompatible solvent becomes optional. In this embodiment, this invention is directed to a method for endovascular formation of a radioactive stent at a vascular site which method comprises:

(a) endovascularly delivering to a vascular site a liquid permeable balloon catheter, said balloon cathether comprising a balloon membrane at least a portion of which is liquid permeable;

(b) inflating said balloon to contact the vascular walls at said vascular site by delivering thereto a composition, said composition comprising a biocompatible prepolymer, a water insoluble radioisotope and optionally a biocompatible solvent; and (c) in situ forming a radioactive stent at the vascular site by maintaining positive pressure on said balloon wherein at least a portion of said composition permeates through said permeable balloon membrane into the vascular site whereupon the composition forms a solid mass which contacts and adheres to the vascular walls thereby forming a radioactive stent at said vascular site.

Preferably the radioactive fluid composition employed in this aspect of the methods of this invention comprises:

(a) a biocompatible prepolymer;

(b) an optional biocompatible solvent; and (c) from about 0.1 to about 35 weight percent of a water insoluble radioisotope having a radioactive content of from about 0.1 microcuries to about 35 microcuries.

In a preferred embodiment of either of the method aspects, the amount and radioactive content of the radioisotope is sufficient to provide for a cumulative ionizing radiation dosage at the site of implantation in a mammalian subject of from about 3 to about 30 Gray (Gy) as measured at a distance approximately 2 mm away from the vessel wall adjacent the vascular site wherein the stent is formed.

It is, of course, understood that both the activity of the radioactive element and dose of radiation delivered to the vascular site varies may widely due to the requirements of the vascular site, volume of tissue treated, etc. Evaluation of such factors to determine the appropriate activity of the radioactive isotope and the dose of radiation delivered is well within the skill of the art.

In a further preferred embodiment of either of the method aspects, the biocompatible solvent is dimethylsulfoxide (DMSO), ethanol, ethyl lactate or acetone.

In one embodiment, the radioisotope acts as a contrast agent to permit visualization of the composition during delivery (e.g., catheter delivery). Alternatively, a non-radioactive contrast agent is employed in combination with the radioisotope in order to ensure visualization.

Another aspect of this invention is directed to a kit of parts comprising:

(a) a first member which contains a composition comprising a water-insoluble biocompatible polymer and a biocompatible solvent;

(b) a liquid permeable balloon catheter.

The biocompatible polymer employed in this kit can be either a biodegradable polymer or a non-biodegradable polymer but is, preferably, a non-biodegradable polymer.

In an alternative embodiment of this aspect of this invention, the biocompatible polymer can be replaced with a biocompatible prepolymer and, when so used, the presence of the biocompatible solvent becomes optional. In this embodiment, this invention is directed to a kit of parts comprising:

(a) a first member which contains a composition comprising a biocompatible prepolymer;

(b) a liquid permeable balloon catheter.

DETAILED DESCRIPTION OF THE INVENTION

This invention is directed to methods for forming vascular stents in mammals by use of radioactive compositions which methods entail the in vivo delivery of radioactive compositions which are delivered as a fluid to one or more vascular sites. Subsequent solidification of this composition in the tissue results in the formation of a radioactive vascular stent and the delivery of a controlled amount of radiation to inhibit restenosis.

However, prior to discussing this invention in further detail, the following terms will first be defined:

The term "biocompatible polymer" refers to polymers which, in the amounts employed, are non-toxic and substantially non-immunogenic when used internally in the patient and which are substantially insoluble in the body fluid of the mammal. The biocompatible polymer can be either biodegradable or, preferably, non-biodegradable.

Biodegradable polymers are disclosed in the art.[1,3] For example, Dunn, et al.[1] discloses the following examples of biodegradable polymers: linear-chain polymers such as polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), polyvinylpyrrolidone, polyethylene glycol, polyhydroxycellulose, chitin, chitosan, and copolymers, terpolymers and combinations thereof. Other biodegradable polymers include, for example, fibrin, gelatin, collagen, etc.

Suitable non-biodegradable biocompatible polymers include, by way of example, cellulose acetates[2,6-7] (including cellulose diacetate[5]), ethylene vinyl alcohol copolymers[4,8], hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof[9].

Preferably, the biocompatible polymer employed does not cause an adverse inflammatory reaction when employed in vivo. The particular biocompatible polymer employed is selected relative to the viscosity of the resulting polymer solution, the solubility of the biocompatible polymer in the biocompatible solvent, and the like. For example, the selected biocompatible polymer should be soluble in the amounts employed in the selected biocompatible solvent and the resulting composition should have a viscosity suitable for in vivo delivery by, e.g., injection. Such factors are well within the skill of the art.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by merely adjusting the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. For ease of injection, the ethylene vinyl alcohol copolymer composition is preferably selected such that a solution of 5 weight percent of the ethylene vinyl alcohol copolymer, 20 weight percent of a tantalum contrast agent in DMSO has a viscosity equal to or less than 60 centipoise at 20° C. As is apparent to one skilled in the art, with all other facts being equal, copolymers having a lower molecular weight will impart a lower viscosity to the composition as compared to higher molecular weight copolymers. Accordingly, adjustment of the viscosity of the composition as necessary for catheter delivery can be readily achieved by merely adjusting the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous environment (e.g., blood or tissue). In a particularly preferred embodiment, the copolymers employed herein comprise a mole percent of ethylene of from about 25 to about 60 and a mole percent of vinyl alcohol of from about 40 to about 75. Even more preferably, the copolymers employed herein comprise a mole percent of ethylene of from about 38 to about 48 and a mole percent of vinyl alcohol of from about 52 to 62. These compositions provide for requisite precipitation rates suitable for use in the methods described therein.

The term "contrast agent" refers to a biocompatible radiopaque material capable of being monitored during injection into a mammalian subject by, for example, radiography. The contrast agent can be either water soluble or water insoluble and preferably does not contain radioactivity above the native or endogenous amounts naturally occurring in the elements employed (i.e., are "non-radioactive").

Examples of water soluble contrast agents include metrizamide, iopamidol, iothalamate sodium, iodomide sodium, and meglumine.

Examples of water insoluble contrast agents include tantalum, tantalum oxide, and barium sulfate, each of which is commercially available in the proper form for in vivo use including a preferred particle size of about 10 $\mu$m or less. Other water insoluble contrast agents include gold, tungsten, and platinum powders.

Preferably, the contrast agent is water insoluble (i.e., has a water solubility of less than 0.01 mg/ml at 20° C.).

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, ethyl lactate, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide.

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

The term "biocompatible prepolymer" refers to materials which polymerize in situ to form a polymer and which, in the amounts employed, are non-toxic and substantially non-immunogenic when used internally in the patient and which are substantially insoluble in blood. Suitable biocompatible prepolymers include, by way of example, urethanes, cyanoacrylates[10,11,12], (C1-C6)hydroxyalkyl (C1-C6) alkacrylate (e.g., hydroxyethyl methacrylate), silicone prepolymers, and the like. The prepolymer can either be a monomer or a reactive oligomer[12]. Preferably, the biocompatible prepolymer does not cause an adverse inflammatory reaction when employed in vivo.

The term "radioisotope" refers to naturally or non-naturally occurring water insoluble radioisotopes conventionally employed in nuclear medicine including, by way of example only, $^{90}$yttrium, $^{192}$iridium, $^{198}$gold, $^{125}$iodine, $^{137}$cesium, $^{60}$cobalt, $^{55}$cobalt, $^{56}$cobalt, $^{57}$cobalt, $^{52}$magnesium, $^{55}$iron, $^{32}$phosphorus, and $^{90}$strontium. Other radionuclides currently being produced for use in nuclear medicine include, for example, $^{81}$rubidium, $^{206}$bismuth, $^{67}$gallium, $^{77}$bromine, $^{129}$cesium, $^{73}$selenium, $^{72}$selenium, $^{72}$arsenic, $^{103}$palladium, $^{203}$lead, $^{111}$indium, $^{52}$iron, $^{167}$thulium, $^{57}$nickel, $^{62}$zinc, $^{61}$copper, $^{201}$thallium, and $^{123}$iodine. Each of these isotopes can be made by standard techniques well known in the art. Additionally, radioisotopes which are water soluble or water reactable are typically used as water insoluble salts, including, for example, organic slats thereof such as acetate salts, propionate salts, etc. It is understood that the term "radioisotope" includes the elemental isotopes as well as inorganic and organic salts, complexes and/or compounds thereof.

In one embodiment, radioisotopes having a sufficiently high atomic number so as to be radiopaque can be used to serve both as a source of radiation and as a water insoluble contrast agent for detection under fluoroscopy.

In another embodiment, a separate non-radioactive contrast agent is employed in conjunction with the radioisotope.

The term "absorbed dose" or "radiation dose" refers to the dose of radiation typically employed by the attending oncologist to inhibit restenosis. The radiation dose is defined in terms of energy deposited per unit mass, given in the following units: 1 Gray (Gy)=1 Joule per kilogram. In the past, the standard unit of radiotherapy was 1 rad, and 1 Gy=100 rads.

A "stent" is a device which retains integrity of the vascular wall or body lumen when it is placed in contact with or when it is formed adjacent to or in contact with a vascular wall. A stent functions to maintain patency of a body lumen (such as a vascular wall) and is especially used as an implant in blood vessels. Stents may be utilized after atherectomy, which excises plaque, or cutting balloon angioplasty, which scores the arterial wall prior to dilatation, to maintain acute and long-term patency of the vessel. Stents may be utilized in by-pass grafts as well, to maintain vessel patency. Stents can also be used to reinforce collapsing structures in the respiratory, biliary, urological, and other tracts. Effectively, a stent overcomes the natural tendency of the vessel walls of some patients to close back down, thereby maintaining a more normal flow of blood through that vessel than would otherwise be possible if the stent were not in place.

"Restenosis" is the closure of an artery following trauma to the artery caused by efforts to open an occluded portion of the artery, such as, for example, by dilation, ablation, atherectomy or laser treatment of the artery. Restenosis is believed to be a natural healing reaction to the injury of the arterial wall that is caused by angioplasty procedures. The healing reaction begins with the clotting of blood at the site of the injury. The final result of the complex steps of the healing process is intimal hyperplasia, the migration and proliferation of medial smooth muscle cells, until the artery is again stenotic or occluded.

The term "inhibiting restenosis" or "inhibit restenosis" means that restenosis is inhibited from occurring or is reduced or less pronounced in its effect. In other words, the extent of restenosis is reduced, decreased or eliminated.

A "liquid permeable balloon" is a balloon which comprises at least a portion of a permeable balloon membrane which membrane allows the passage, under positive pressure, of a composition comprising a biocompatible polymer, a biocompatible solvent and a radioisotope. The permeable balloon membrane is preferably selected to allow the passage of insoluble particles having a particle size no larger than 10 µm. The positive pressure employed is preferably at least 5 atmospheres, more preferably 5 to 75 atmospheres, and still more preferably 10 to 50 atmospheres. The permeable material employed in the balloon is not critical provided that it meets the above criteria. Such materials include, by way of example, expanded polytetrafluoroethylene (PTFE, tradename Gortex™) and polyethyleneterephthalate (Dacron™, DuPont, Wilmington, Del.).

Compositions

The polymer or prepolymer compositions employed in the methods of this invention are preferably first prepared without radioactive agents by conventional methods whereby each of the components is added and the resulting composition mixed together until the overall composition is substantially homogeneous.

Suitable radioactive compositions are described, for example, by Greff, et al.[14]

For example, polymer compositions can be prepared by adding sufficient amounts of the biocompatible polymer to the biocompatible solvent to achieve the effective concentration for the polymer composition. Preferably, the polymer composition will comprise from about 2.5 to about 8.0 weight percent of the biocompatible polymer composition based on the total weight of the polymer composition and more preferably from about 4 to about 5.2 weight percent. If necessary, gentle heating and stirring can be used to effect dissolution of the biocompatible polymer into the biocompatible solvent, e.g., 12 hours at 50° C.

Where a separate non-radioactive contrast agent is employed, sufficient amounts of this contrast agent are then added to the biocompatible solvent to achieve the effective concentration for the complete composition. Preferably, the composition will comprise from about 7 to about 40 weight percent of total contrast agent (non-radioactive contrast agent plus any radiopaque radioisotope) and more preferably from about 14 to about 30 weight percent and even more preferably about 22 weight percent.

The biocompatible solvent preferably comprises from about 40 to about 90 weight percent of the composition based on the total weight of the composition and more preferably about 50 to about 90 weight percent.

When a water soluble non-radioactive contrast agent is employed, the agent is typically soluble in the solution comprising the non-aqueous solvent and stirring is effected to render the composition homogeneous.

When a water insoluble non-radioactive contrast agent is employed, the agent is insoluble in the biocompatible solvent, and stirring is employed to effect homogeneity of the resulting suspension. In order to enhance formation of the suspension, the particle size of the water insoluble non-radioactive contrast agent is preferably maintained at about 10 μm or less and more preferably at from about 1 to about 5 μm (e.g., an average size of about 2 μm).

In one embodiment, a non-radioactive contrast agent having a particle size of less than 10 μm is prepared, for example, by fractionation. In such an embodiment, a non-radioactive water insoluble contrast agent such as tantalum, having an average particle size of less than about 20 μm, is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition can be heat sterilized and then stored preferably in sealed bottles or vials until needed.

Each of the polymers recited herein is commercially available or can be prepared by methods well known in the art. For example, polymers are typically prepared by conventional techniques such as radical, thermal, UV, γ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the biocompatible solvent, the polymers described herein are preferably not cross-linked.

Prepolymer compositions can be prepared by adding sufficient amounts of any non-radioactive contrast agent employed in the liquid (e.g., liquid prepolymer) to achieve the effective concentration for the complete polymer composition. Preferably, the total contrast agent (non-radioactive contrast agent plus any radiopaque radioisotope) will comprise from about 7 to about 40 weight percent of the prepolymer composition based on the total weight of the composition and more preferably from about 14 to about 30 weight percent and even more preferably about 22 weight percent.

When a non-radioactive contrast agent is used which is not soluble in the biocompatible prepolymer composition, stirring is employed to effect homogeneity of the resulting suspension. In order to enhance formation of the suspension, the particle size of the insoluble non-radioactive contrast agent is preferably maintained at about 10 μm or less and more preferably at from about 1 to about 5 μm (e.g., an average size of about 2 μm).

When the prepolymer is liquid (as in the case of cyanoacrylates or silicone), the use of a biocompatible solvent is not strictly necessary but may be preferred to provide for an appropriate viscosity, for an appropriate curing time, etc. in the composition. Preferably, when employed, the biocompatible solvent will comprise from about 30 to about 90 weight percent of the biocompatible prepolymer composition based on the total weight of the prepolymer composition and more preferably from about 60 to about 80 weight percent. When a biocompatible solvent is employed, the prepolymeric composition typically comprises from about 10 to about 50 weight percent of the prepolymer based on the total weight of the composition.

Suitable solvents include iodinated soy bean or poppy seed oil for cyanoacrylates and water for hydroxyacrylics such as hydroxyethyl methacrylate. In such cases, the oil acts both as a carrier for the prepolymer, a contrast agent and a polymerization time modifier. Other solvents include hexamethyldisiloxane which is preferably employed in conjunction with silicone.

In a particularly preferred embodiment, the prepolymer is a cyanoacrylate which is preferably employed in a 1:1 ratio with an iodinated oil. When so employed, the cyanoacrylate adhesive is selected to have a viscosity of from about 5 to about 40 centipoise at 20° C.

The radioisotope is preferably added to the otherwise complete composition immediately prior to the administration of the composition to the patient in order to reduce exposure of radiation to the clinician. In a preferred embodiment, the radioisotope is $^{192}$iridium, $^{198}$gold, $^{125}$iodine, $^{137}$cesium or $^{60}$cobalt. The radioisotope and its activity is preferably selected relative to the size and location of the vascular site in the patient. This material may also be used as part of or the entire contrast agent to aid in the placement of the composition, usually by fluoroscopy, to form the radioactive stent.

Treatment dosages of radiation employed in a particular patient are, of course, dependent upon the judgment of the attending clinician and nuclear medicine professional depending upon factors such as the type and size of the vascular site in the patient, the age, weight and general condition of the patient, the toxicity and/or side effects due to the radiation treatment and the like. Such factors are well known to the skilled artisan.

In any event, in this embodiment, sufficient levels of radiation are employed to effect inhibition of restenosis.

In view of the above, the compositions described herein preferably comprise from about 0.1 to about 35 weight percent of a water insoluble radioisotope having from a radioactive content of from about 0.1 microcurie to about 35 microcurie. In another preferred embodiment, the amount and radioactive content of the radioisotope is sufficient to provide for a cumulative ionizing radiation dosage at the site of implantation in a mammalian subject of from about 3 to 30 Gray (Gy).

The solid mass formed by the methods of this invention is permanently placed within the patient.

Methods

The compositions described above can be employed in the formation of a radioactive stent at a vascular site in mammals. The treatment protocol includes assessing the vascular site, determine the total radiation activity needed to inhibit restenosis and determine the vascular site or sites to deliver the compositions. Each of these steps is well known in the art.

The methods described herein employ conventional endovascular catheter techniques to provide a permeable balloon at the vascular site. Once the permeable balloon is placed at the selected vascular site, positive pressure in created within the balloon which inflates the balloon wherein the permeable balloon membrane contacts the vascular wall. Such positive pressure is preferably generated in the form of injecting a fluid composition comprising a water insoluble biocompatible polymer, a biocompatible solvent and a radioisotope. Once inflated, the balloon is maintained under physiological conditions for a period of time to permit a portion of the fluid composition to permeate the balloon membrane and invade the vascular site defining the stenotic region.

When the fluid composition is introduced in vivo at this vascular site, the biocompatible solvent diffuses rapidly into the body fluid and a solid, non-migratory precipitate or solid mass forms which precipitate is the water insoluble polymer and radioisotope encapsulated therein as well as any non-radioactive water insoluble contrast agent. Without being limited to any theory, it is believed that initially, solid mass forms upon contact with the body fluid.

When a prepolymeric composition is introduced in vivo, the prepolymer rapidly polymerizes in situ (preferably in less than 15 minutes and more preferably in less than 5 minutes) and a solid non-migratory mass forms which mass is the water insoluble polymer and radioisotope encapsulated therein as well as any non-radioactive water insoluble contrast agent.

In either case, a solid non-migratory radioactive mass in situ forms a radioactive stent in the vascular site. The size and thickness of the stent formed relate directly to the size and permeability of the balloon selected as well as the extent and duration of positive pressure maintained on the inflated balloon. Such factors are well within the skill of the art. Preferably, the stent thicknesses formed by the methods of this invention range from about 0.05 mm to about 0.5 mm. In addition, the radiation employed in the composition results in inhibition of restenosis. Preferably, the radiation employed ranges from 0.1 to 35 microcuries. In a further preferred embodiment, the amount and radioactive content of the radioisotope is sufficient to provide for a cumulative ionizing radiation dosage at the site of implantation in a mammalian subject of from about 3 to about 30 Gy.

Kits of Parts

Another embodiment of this invention is a kit of parts comprising a water-insoluble biocompatible polymer, a biocompatible solvent, a liquid permeable balloon and a catheter suitable for delivering said balloon intravascularly. At the appropriate point in time the composition comprising the biocompatible polymer and biocompatible solvent can be mixed, together with an appropriate radioactive isotope. In a preferred embodiment, the biocompatible solvent is dimethylsulfoxide or ethyl lactate.

In an alternative embodiment, the kit of parts comprises a biocompatible prepolymer, a liquid permeable balloon and a catheter suitable for delivering said balloon intravascularly. At the appropriate point in time the composition comprising the biocompatible prepolymer can be mixed with an appropriate radioactive isotope.

Utility

The methods described herein are useful in the in situ formation of radioactive vascular stents. In these methods, a fluid composition is delivered to a vascular site by known endovascular catheter techniques in a sufficient amount to form a stent in vivo, in other words, to repave the vascular site. In addition, the level of radiation employed in the fluid composition delivered is sufficient to inhibit restenosis of the vascular site. Accordingly, these compositions find use in human and other mammalian subjects requiring a radioactive vascular stent.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

cc=cubic centimeter
DMSO=dimethylsulfoxide
EVOH=ethylene vinyl alcohol copolymer
g=gram
Gy=gray (units for dose of radiation; 1 Gy=1 J per kg=100 rads)
kg=kilogram
mg=milligram
mL=milliliter
OD=outer diameter
ppm=parts per million
$\mu$Ci=microCurie
$\mu$m=micron Example 1

The purpose of this example is to demonstrate the preparation of polymer compositions useful in this invention. These compositions were prepared using "cold" isotopes in order to illustrate the compatibility of the compositions and suitability for delivery in vivo. It is understood that "hot" compositions could be similarly prepared.

Specifically, an EVOH polymer composition was prepared as follows:

Composition 0.396 g EVOH (48 mole percent ethylene);
1.485 g micronized tantalum; and
4.95 mL DMSO.

After dissolution of the polymer at 50° C., 3 cc of this composition was then added to 0.03 g iridium powder (Aldrich Chemical Company, Milwaukee, Wis., USA, Catalog No. 20968-6, 99.9% purity, screened to <25 $\mu$m) to provide for a suspension comprising 0.4% by weight iridium ("cold" or non-radioactive). The resulting composition was then shaken for 4 minutes to disperse the insoluble materials. Immediately, 0.8 cc of the suspension was withdrawn via a 1 cc syringe through a 21 gauge needle. Three 0.1 cc aliquots were then injected into an excess of normal saline maintained at about 37° C. to generate the precipitate. The saline was then stirred for about 10 minutes whereupon the precipitate was examined for inner/outer consistency. In each case, a solid coherent precipitate formed in the saline.

The procedure set forth above was repeated twice. In the first instance, the amount of tantalum powder was changed to 14 weight percent and the amount of iridium powder was increased to 6 weight percent. In the second instance, the tantalum powder was removed from the composition and the amount of iridium adjusted to 20 weight percent. In each case, the total amount of tantalum/iridium was about 20 weight percent.

Both compositions, upon injection into saline, provided a solid coherent precipitate.

Example 2

The purpose of this example is to demonstrate the preparation of a prepolymer composition useful in this invention. This compositions was prepared using "cold" isotopes in order to illustrate the compatibility of the composition and suitability for delivery in vivo. It is understood that "hot" compositions could be similarly prepared.

Specifically, a cyanoacrylate prepolymer composition was prepared by adding 500 mg of iridium non-radioactive powder (Aldrich Chemical Company, Milwaukee, Wis., USA, Catalog No. 20968-6, 99.9% purity, screened to <25

μm) to 2 g n-butyl cyanoacrylate containing 100 ppm $SO_2$ as a stabilizer to yield a composition comprising 20% by weight of iridium. The ingredients mixed well, yielding a black/gray suspension. The iridium settled within several seconds after mixing, so constant, gentle agitation was required. In this regard, a higher viscosity cyanoacrylate composition (e.g., a cyanoacrylate oligomer) could be used to prolong the suspension time of the iridium or, alternatively, a smaller particle size of the iridium can be used.

The mixture remained liquid with no signs of premature polymerization when evaluated at one hour after mixing and again after 12 days thereby evidencing that the iridium was compatible in this composition.

About 0.2 cc of this composition was taken up in a 1 cc syringe through a 21 gage needle and injected into about 150 cc of an aqueous solution of 0.1 N $NaHCO_3$ to simulate a tissue environment and cure the prepolymer. Upon injection, three small black/gray droplets were formed which immediately fell to the bottom of the container. It took about 15 minutes for the cyanoacrylate to fully cure and to be tack free.

The procedure set forth above was repeated with n-butyl cyanoacrylate alone (i.e., without the iridium) and the cyanoacrylate cured in approximately the same time evidencing that the iridium was compatible with the cyanoacrylate.

Example 3

The purpose of this example is to illustrate how to deliver the composition of either Example 1 or 2 to a vascular site of a mammal. This example employs a dog with atherosclerosis.

Specifically, a juvenile domestic swine (25 kg) is selected for use in this example. The animal is prepared for a known angioplasty procedure. Through a femoral access, a PTCA balloon catheter is placed into the left anterior descending coronary artery and inflated 3 times at 12 atmospheres. The balloon is 30% greater in diameter than the artery at this point. This catheter is then removed.

At this time, 1.0 mL of a 0.4% iridium composition described in Example 1 above (except that the iridium has a radioactive content of 15 μCi) is shaken to ensure homogeneity and then loaded into a 1 cc syringe. A porous balloon catheter, such as one known in the art, is positioned at a vascular site within the artery with the aid of fluoroscopy to ensure proper positioning and approximately 0.01 mL of this composition is injected therein through the liquid permeable balloon. Upon introduction into the vascular site, a solid coherent precipitate forms a radioactive stent which comprises the polymer, the contrast agent and the iridium which stents the artery and inhibits restenosis.

Over 30 days, the amount of radiation delivered internally to the vascular site of the swine is about 15 Gray.

From the foregoing description, various modifications and changes in the composition and method will occur to those skilled in the art. All such modifications coming within the scope of the appended claims are intended to be included therein.

What is claimed is:

1. A method for endovascular formation of a radioactive stent at a vascular site which method comprises:
   (a) endovascularly delivering to a vascular site a liquid permeable balloon catheter, said balloon cathether comprising a balloon membrane at least a portion of which is liquid permeable;
   (b) inflating said balloon to contact the vascular walls at said vascular site by delivering thereto a composition, said composition comprising a biocompatible polymer, a biocompatible solvent and a water insoluble radioisotope; and
   (c) in situ forming a radioactive stent at the vascular site by maintaining positive pressure on said balloon wherein at least a portion of said composition permeates through said permeable balloon membrane into the vascular site whereupon the composition forms a solid mass which contacts and adheres to the vascular walls thereby forming a radioactive stent at said vascular site.

2. The method according to claim 1 wherein said biocompatible solvent is selected from the group consisting of dimethylsulfoxide, ethanol, ethyl lactate and acetone.

3. The method according to claim 2 wherein said biocompatible solvent is dimethylsulfoxide.

4. The method according to claim 1 wherein said water-insoluble biocompatible polymer is selected from the group consisting of biodegradable and non-biodegradable polymers.

5. The method according to claim 4 wherein said water-insoluble biocompatible polymer is non-biodegradable.

6. The method according to claim 5 wherein said non-biodegradable biocompatible polymer is selected from the group consisting of cellulose acetates, ethylene vinyl alcohol copolymers, hydrogels, polyacrylonitrile, polyvinylacetate, cellulose acetate butyrate, nitrocellulose, copolymers of urethane/carbonate, copolymers of styrene/maleic acid, and mixtures thereof.

7. The method according to claim 6 wherein said non-biodegradable biocompatible polymer is a copolymer of ethylene and vinyl alcohol.

8. The method according to claim 4 wherein said water-insoluble biocompatible polymer is biodegradable.

9. The method according to claim 8 wherein said biodegradable biocompatible polymer is a linear-chain polymer selected from the group consisting of polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), polyvinylpyrrolidone, polyethylene glycol, polyhydroxycellulose, chitin, chitosan, copolymers, terpolymers thereof, gelatin, fibrin and collagen.

10. The method according to claim 1 wherein said radioisotope is selected from the group consisting of $^{90}$yttrium, $^{192}$iridium, $^{198}$gold, $^{125}$iodine, $^{137}$cesium, $^{60}$cobalt, $^{55}$cobalt, $^{56}$cobalt, $^{57}$cobalt, $^{57}$magnesium, $^{55}$iron, $^{32}$phosphorus, $^{90}$strontium, $^{81}$rubidium, $^{206}$bismuth, $^{67}$gallium, $^{77}$bromine, $^{129}$cesium, $^{73}$selenium, $^{72}$selenium, $^{72}$arsenic, $^{103}$palladium, $^{203}$lead, $^{111}$indium, $^{52}$iron, $^{167}$thulium, $^{57}$nickel, $^{62}$zinc, $^{61}$copper, $^{201}$thallium, and $^{123}$iodine.

11. The method according to claim 10 wherein the radioisotope is employed in an amount effective to inhibit restenosis.

12. The method according to claim 1 which further comprises a non-radioactive contrast agent.

13. The method according to claim 12 wherein said non-radioactive contrast agent is water soluble.

14. The method according to claim 13 wherein said water soluble non-radioactive contrast agent is selected from the group consisting of metrizamide, iopamidol, iothalamate sodium, iodomide sodium, and meglumine.

15. The method according to claim 12 wherein said non-radioactive contrast agent is water insoluble.

16. The method according to claim 15 wherein said water insoluble contrast agent is tantalum, tantalum oxide, barium sulfate, tungsten, gold and platinum.

17. The method according to claim 1 wherein said fluidic composition comprises from about 0.1 to about 35 weight percent of a water insoluble radioisotope having from a radioactive content of from about 0.1 microcurie to about 35 microcurie.

18. A method for endovascular formation of a radioactive stent at a vascular site which method comprises:
(a) endovascularly delivering to a vascular site a liquid permeable balloon catheter, said balloon cathether comprising a balloon membrane at least a portion of which is liquid permeable;
(b) inflating said balloon to contact the vascular walls at said vascular site by delivering thereto a composition, said composition comprising a biocompatible prepolymer, a water insoluble radioisotope and optionally a biocompatible solvent; and
(c) in situ forming a radioactive stent at the vascular site by maintaining positive pressure on said balloon wherein at least a portion of said composition permeates through said permeable balloon membrane into the vascular site whereupon the composition forms a solid mass which contacts and adheres to the vascular walls thereby forming a radioactive stent at said vascular site.

19. The method according to claim 18 wherein said biocompatible prepolymer is selected from the group consisting of cyanoacrylates, urethanes, (C1-C6)hydroxyalkyl, (C1-C6)alkacrylate, and silicone prepolymers.

20. The method according to claim 19 wherein said biocompatible prepolymer is a cyanoacrylate.

21. The method according to claim 18 wherein said radioisotope is selected from the group consisting of $^{90}$yttrium, $^{192}$iridium, $^{198}$gold, $^{125}$iodine, $^{137}$cesium, $^{60}$cobalt, $^{55}$cobalt, $^{56}$cobalt, $^{57}$cobalt, $^{57}$magnesium, $^{55}$iron, $^{32}$phosphorus, $^{90}$strontium, $^{81}$rubidium, $^{206}$bismuth, $^{67}$gallium, $^{77}$bromine, $^{129}$cesium, $^{73}$selenium, $^{72}$selenium, $^{72}$arsenic, $^{103}$palladium, $^{203}$lead, $^{111}$indium, $^{52}$iron, $^{167}$thulium, $^{57}$nickel, $^{62}$zinc, $^{61}$copper, $^{201}$thallium, and $^{123}$iodine.

22. The method according to claim 21 wherein said radioisotope is employed in an amount effective to inhibit restenosis.

23. The method according to claim 18 which further comprises a non-radioactive contrast agent.

24. The method according to claim 23 wherein said non-radioactive contrast agent is water soluble.

25. The method according to claim 24 wherein said water soluble non-radioactive contrast agent is selected from the group consisting of metrizamide, iopamidol, iothalamate sodium, iodomide sodium, and meglumine.

26. The method according to claim 23 wherein said non-radioactive contrast agent is water insoluble.

27. The method according to claim 26 wherein said water insoluble contrast agent is tantalum, tantalum oxide, barium sulfate, tungsten, gold and platinum.

* * * * *